(12) United States Patent
Cho

(10) Patent No.: US 9,576,105 B2
(45) Date of Patent: Feb. 21, 2017

(54) METHOD OF DISPLAYING HEALTH INFORMATION AND ELECTRONIC DEVICE FOR PROVIDING SAME

(71) Applicant: Samsung Electronics Co., Ltd., Gyeonggi-do (KR)

(72) Inventor: Jeeyun Cho, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/634,511

(22) Filed: Feb. 27, 2015

(65) Prior Publication Data
US 2015/0248535 A1    Sep. 3, 2015

(30) Foreign Application Priority Data

Feb. 28, 2014   (KR) .................. 10-2014-0024623

(51) Int. Cl.
*A61B 5/00*      (2006.01)
*G01C 22/00*   (2006.01)
*G06F 19/00*   (2011.01)

(52) U.S. Cl.
CPC ....... *G06F 19/3406* (2013.01); *G06F 19/3481* (2013.01); *G06F 19/3487* (2013.01)

(58) Field of Classification Search
USPC ............. 235/379; 702/189, 160; 340/870.09
See application file for complete search history.

(56) References Cited

U.S. PATENT DOCUMENTS

| 2014/0156228 A1* | 6/2014 | Molettiere | G06F 19/322 702/189 |
| 2014/0197965 A1* | 7/2014 | Park | G08B 21/18 340/870.09 |

FOREIGN PATENT DOCUMENTS

KR    10-2010-0025300    3/2010

* cited by examiner

*Primary Examiner* — Daniel Hess

(57) ABSTRACT

Disclosed is a method of displaying health information by an electronic device. The method includes: activating an application providing at least one piece of health-related information; identifying a user account pre-stored in the application and receiving health state measurement data of the user account; receiving pieces of health state measurement data of similar group accounts from a host device; determining an account with which to be compared among the similar group accounts based on a predetermined reference and identifying health state measurement data of the account with which to be compared; and displaying the health state measurement data of the user account and the health state measurement data of the account with which to be compared.

15 Claims, 11 Drawing Sheets

METHOD OF DISPLAYING HEALTH INFORMATION AND ELECTRONIC DEVICE FOR PROVIDING SAME

CROSS-REFERENCE TO RELATED APPLICATION(S) AND CLAIM OF PRIORITY

The present application is related to and claims priority from and the benefit under 35 U.S.C. §119(a) of Korean Patent Application No. 10-2014-0024623, filed on Feb. 28, 2014, which is hereby incorporated by reference for all purposes as if fully set forth herein.

TECHNICAL FIELD

The present application relates generally to a method of displaying health information and an electronic device for providing the same, and more particularly to a method of displaying health information that provides a user interface related to health and an electronic device providing the same.

BACKGROUND

As people increasingly become interested in health, demand for identifying a health state using various health measurement devices has recently increased. Accordingly, various devices for measuring health have appeared. For example, the devices for measuring health include a blood pressure measuring device, a pulse measuring device, a momentum measuring device, a skin current measuring device, and a body temperature measuring device, and a health measuring device are installed and used in a portable terminal.

People also use a health application to check their own health states. However, when the user uses a health application, the health application displays only data corresponding to basic health information of the user and, thus, the user cannot help but use delayed feedback to deal with changes in the health measurement data. Further, when the user uses the health application, the compatibility with a device for measuring health is low, and accordingly, the user receives delayed feedback in real time. In addition, it is difficult to compare health data of the user with health data of another user, and, thus, also difficult to recognize an objective average health state index of users in a group.

SUMMARY

To address the above-discussed deficiencies, it is a primary object to provide a method of displaying health information and an electronic device for providing the same to solve the above problems.

In accordance with an aspect of the present disclosure, a method of displaying health information by an electronic device is provided. The method includes: activating an application providing at least one piece of health-related information; identifying a user account pre-stored in the application and receiving health state measurement data of the user account; receiving pieces of health state measurement data of similar group accounts from a host device; determining an account with which to be compared among the similar group accounts based on a predetermined reference and identifying health state measurement data of the account with which to be compared; and displaying the health state measurement data of the user account and the health state measurement data of the account with which to be compared.

According to an embodiment of the present disclosure, the user can identify a more specific health state through displayed body information and health state measurement information of the user.

Further, according to an embodiment of the present disclosure, the user can identify a health rank of the user in all groups by comparing a user health state with meaningful group health states.

In addition, according to an embodiment of the present disclosure, the user can more conveniently and enjoyably analyze the health state through a user interface for comparing and analyzing health states of the user and other users.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
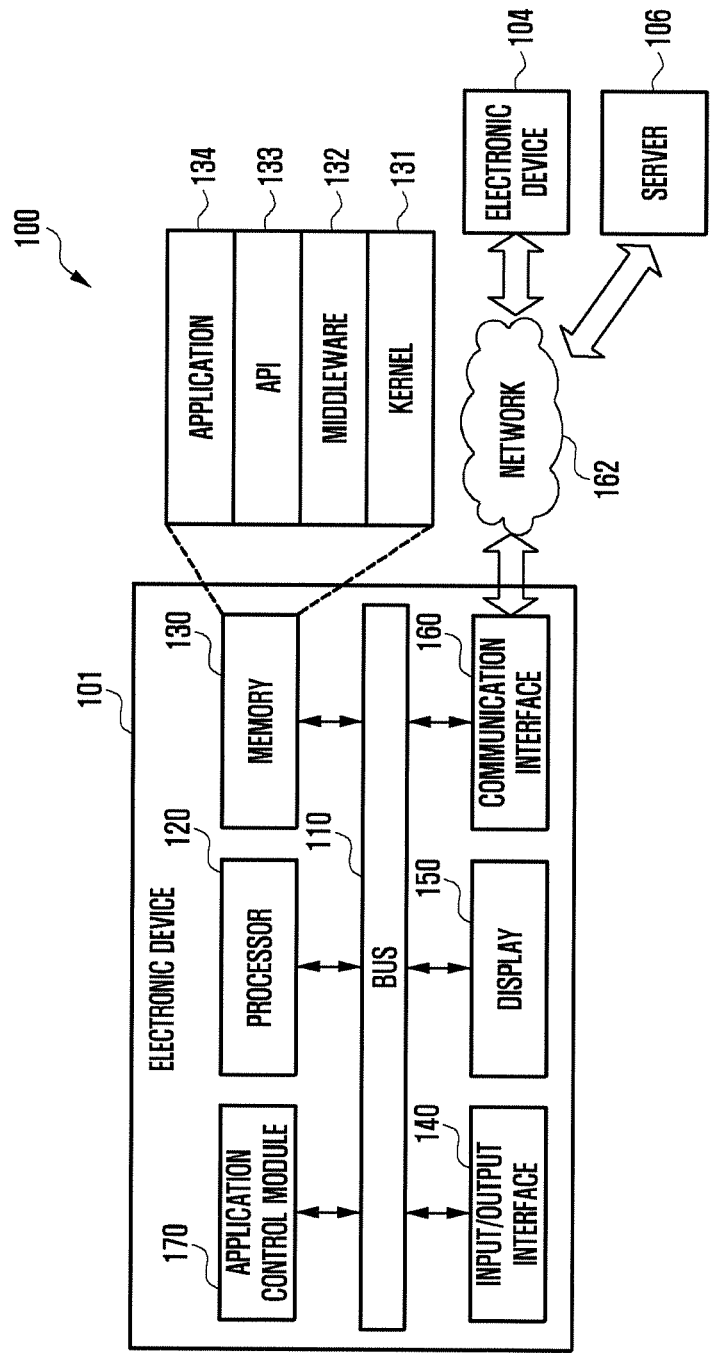
FIG. 1 illustrates a network environment including an electronic device according to embodiments of the present disclosure.

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged wireless communication device. Hereinafter, the present disclosure will be described with reference to the accompanying drawings. The present disclosure may have various modifications and embodiments and thus will be described in detail with reference to specific embodiments illustrated in the drawings. However, it should be understood that there is no intent to limit the present disclosure to the particular forms disclosed herein; rather, the present disclosure should be construed to cover all modifications, equivalents, and/or alternatives falling within the spirit and scope of the disclosure. In the description of the drawings, identical or similar reference numerals are used to designate identical or similar elements.

It will be understood that the expressions "comprises" and "may comprise" is used to specify presence of disclosed function, operation, component, and so forth, but do not preclude the presence of one or more functions, operations, components, and so forth. It will be further understood that the terms "comprises" or "has" when used in this specification, specify the presence of stated feature, number, step, operation, component, element, or a combination thereof but do not preclude the presence or addition of one or more other features, numbers, steps, operations, components, elements, or combinations thereof. In the present disclosure, the expression "and/or" is taken as specific disclosure of each and any combination of enumerated things. For example, A and/or B is to be taken as specific disclosure of each of A, B, and A and B.

As used herein, teens such as "first," "second," and so forth, are used to describe various components, however, it is obvious that the components should not be defined by these terms. For example, the terms do not restrict the order and/or importance of the corresponding components. The terms are used only for distinguishing one component from another component. For example, a first component can be referred to as a second component and likewise, a second component may also be referred to as a first component, without departing from the teaching of the inventive concept.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present.

The terminology used herein is for the purpose of describing particular embodiments only and is not intended to be limiting of the disclosure. As used herein, the singular forms "a", "an" and "the" are intended to include the plural forms as well, unless the context clearly indicates otherwise.

Unless otherwise defined herein, all terms including technical or scientific terms used herein have the same meanings as commonly understood by those skilled in the art to which the present disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

According to various embodiments of the present disclosure, the electronic device can include devices having an operation support function. Examples of the electronic device can include smartphone, table Personal Computer (PC), mobile phone, video phone, electronic book (e-book) reader, desktop PC, laptop PC, netbook computer, Personal Digital Assistant (PDA), Portable Multimedia Player (PMP), MP3 player, mobile medical appliance, camera, wearable device (y head-mounted device (HMD) such as electronic glasses, electronic clothing, electronic bracelet, electronic necklace, electronic appcessory, electronic tattoo, smartwatch, etc.

According to certain embodiments, the electronic device can be one of smart home appliances having operation support function. Examples of the smart electronic appliance as an electronic device can include television, Digital Video Disk (DVD) player, audio player, refrigerator, air-conditioner, vacuum cleaner, electronic oven, microwave oven, laundry machine, air cleaner, set-to box, TV box (for example, a SAMSUNG HOMESYNC, APPLE TV, and GOOGLE TV), game console, electronic dictionary, electronic key, camcorder, and electronic frame, and the like.

According to certain embodiments, examples of the electronic device can include medical device (such as, Magnetic Resonance Angiography (MRA), Magnetic Resonance Imaging (MRI), Computed Tomography (CT)), Navigation device, Global Positioning System (GPS) receiver, Event Data Recorder (EDR), Flight Data Recorder (FDR), car infotainment device, maritime electronic device (such as, maritime navigation device and gyro compass), aviation electronic device (avionics), security device, vehicle head unit, industrial or home robot, Automatic Teller's Machine (ATM) of financial institution, Point Of Sales (POS), and the like.

According to certain embodiments, examples of the electronic device include furniture and buildings, or structures, having a communication function, electronic board, electronic signature receiving device, projector, and metering device, such as water, electric, gas, and electric wave metering devices. According to various embodiments, the electronic device can be any combination of the aforementioned devices. According to various embodiments of the present disclosure, the electronic device can be a flexible device. It is obvious to those skilled in the art that the electronic device is not limited to the aforementioned devices.

Descriptions are made of the electronic devices according to various embodiments with reference to accompanying drawings hereinafter. The term 'user' used in various embodiments may denote a person or a device, such as an artificial intelligent electronic device, using the electronic device.

In certain embodiments of the present disclosure, the term 'object screen' denotes the screen including execution icons of applications installed in the electronic device, favorite webpage icons, folders, files, images, and the like. In certain embodiments of the present disclosure, the object screen includes at least one tab screen, for example, a 'recent' tab screen, 'object' tab screen, 'download' tab screen, and 'recommend' tab screen. The objects can be presented differently depending upon the tab screen. More particularly, the recent tab screen can be the screen for displaying the objects running or having execution history. The object tab screen can be the screen presenting the objects installed in the electronic device that are arranged according to the user setting. The download tab screen can be the screen presenting the objects installed in the electronic device. The 'recommend' tab screen presents the objects recommended based on the information on the objects executed by user.

FIG. 1 illustrates a network environment including electronic devices. The electronic device 101 includes a bus 110, a processor 120, a memory 130, an input/output interface 140, a display 150, a communication interface 160, and an application control module 170.

The bus 110 connects the aforementioned components to each other. The bus 110 is a circuit for exchanging signals, such as control messages, among the components.

For example, the processor 120 receives a command from any of the aforementioned components, such as memory 130, input/output interface 140, display 150, communication interface 160, and application control module 170, through the bus 110, interprets the command, and executes operation or data processing according to the decrypted command.

The memory 130 stores the command or data received from the processor 120 or other components, such as input/output interface 140, display 150, communication interface 160, application control module 170, and so forth, or generated by the processor 120 or other components. The memory 130 stores program modules including kernel 131, middleware 132, Application Programming Interface (API) 133, applications 134, and the like. Each programming module can be implemented as software, firmware, hardware, and any combination thereof.

The kernel 131 controls or manages the system resources, such as bus 110, processor 120, and memory 130, for use in executing the operation or function implemented with the middleware 132, the API 133, or the application 134. The kernel 131 also provides an interface allowing the middleware 132, API 133, or application 134 to access the components of the electronic device 101 to control or manage.

The middleware 132 operates as a relay of data communicated between the API 133 or application 134 and the kernel 131. The middle 132 executes control of the task requests from the applications 134 in such a way of assigning priority for use of the system resource, such as bus 110, processor 120, and memory 130, of the electronic device to at least one of the applications 134.

The API 133 is the interface for the applications 134 to control the function provided by the kernel 131 or the middleware 132 and includes at least one interface or function (e.g. command) for file control, window control, image control, or text control.

According to various embodiments, the applications 134 includes Short Messaging Service/Multimedia Messaging Service (SMS/MMS) application, email application, calendar application, alarm application, health care application, such as an application of measuring quantity of motion or blood sugar level, and environmental information application such as an atmospheric pressure, humidity, and temperature applications. Additionally or alternatively, the application 134 can be an application related to information exchange between the electronic device 101 and another external electronic device, such as electronic device 104. Examples of the information exchange application include a notification relay application for relaying specific information to the external electronic device and a device management application for managing the external electronic device.

For example, the notification relay application can be provided with a function of relaying the alarm information generated by the other applications such as an SMS/MMS application, email application, health care application, and environmental information application of the electronic device 101 to an external electronic device, for example, electronic device 104. Additionally or alternatively, the notification relay application can provide the user with the notification information received from an external electronic device, such as electronic device 104. The electronic device application manages, namely installs, deletes, and updates, the function of an external electronic device (for example turn-on/off of the electronic device 104 itself (or a part of it) or adjustment of the brightness, or resolution of the display) that communicates with the electronic device 101 or the service, such as a communication or messaging service, provided by the external electronic device or an application running on the external device.

According to various embodiments, the applications 134 include an application designated according to the property (for example, a type) of an external electronic device, such as electronic device 104. If the external electronic device is the MP3 player, the applications 134 can include a music playback application. Similarly, if the external electronic device is a mobile medical appliance, the applications 134 can include a heal care application. According to an embodiment, the application 134 includes at least one of: applications designated to the electronic device 101; or applications received from the external electronic device, such as from server 106 and electronic device 104.

The input/output interface 140 delivers the command or data input by the user through with an input/output device such as, a sensor, keyboard, and touchscreen, to the processor 120, memory 130, communication interface 160, and/or application control module 170 through the bus 110. For example, the input/output interface 140 provides the processor 120 with the data corresponding to the touch by the user on the touchscreen. The input/output interface 140 outputs the command or data, which is received from the processor 120, memory 130, communication interfaced 160, or the application control module 170 through the bus 110, through the input/output device, for example speaker and display. For example, the input/out interface 140 outputs the voice data processed by the processor 120 to the user through the speaker.

The display 150 presents various information, such as, for example multimedia data and text data, to the user.

The communication interface 160 establishes a communication connection of the electronic device 101 with an external device, such as electronic device 104 and server 106. For example, the communication interface 160 connects to the network 162 through a wireless or wired link for communication with the external device. Examples of the wireless communication technology can include wireless fidelity (Wi-Fi), BLUETOOTH (BT), Near Field Communication (NFC), Global Positioning System (GPS), and cellular communication technology, such as for example Long Term Evolution (LTE), LTE-Advanced (LTE-A), Code Division Multiple Access (CDMA), Wideband CDMA (WCDMA), Universal Mobile Telecommunication System (UMTS), Wireless-Broadband (WiBro), and General System for Mobile communications (GSM). Examples of the wired communication technology include Universal Serial Bus (USB), High Definition Multimedia Interface (HDMI), Recommended Standard 232 (RS-232), and Plain Old Telephone Service (POTS).

According to certain embodiments, the network 162 is a telecommunication network. The communication network includes at least one of a computer network, Internet, Internet of Things, and telephone network. According to certain embodiments, the communication protocol between the electronic device 101 and an external device (for example transport layer protocol, data link layer protocol, and physical layer protocol) can be supported by at least one of the applications 134, API 133, middleware 132, kernel 131, and communication interface 160.

The application control module 170 processes information obtained from other components (for example processor 120, memory 130, input/output interface 140, display 150 and communication interface 160) and provides the processed information to the user in various ways. For example, the application control module 170 identifies an interface element attached to the electronic device 101, store information on the interface element in the memory 130, and activate an application 134 on the basis of the stored information.

Figure 2:
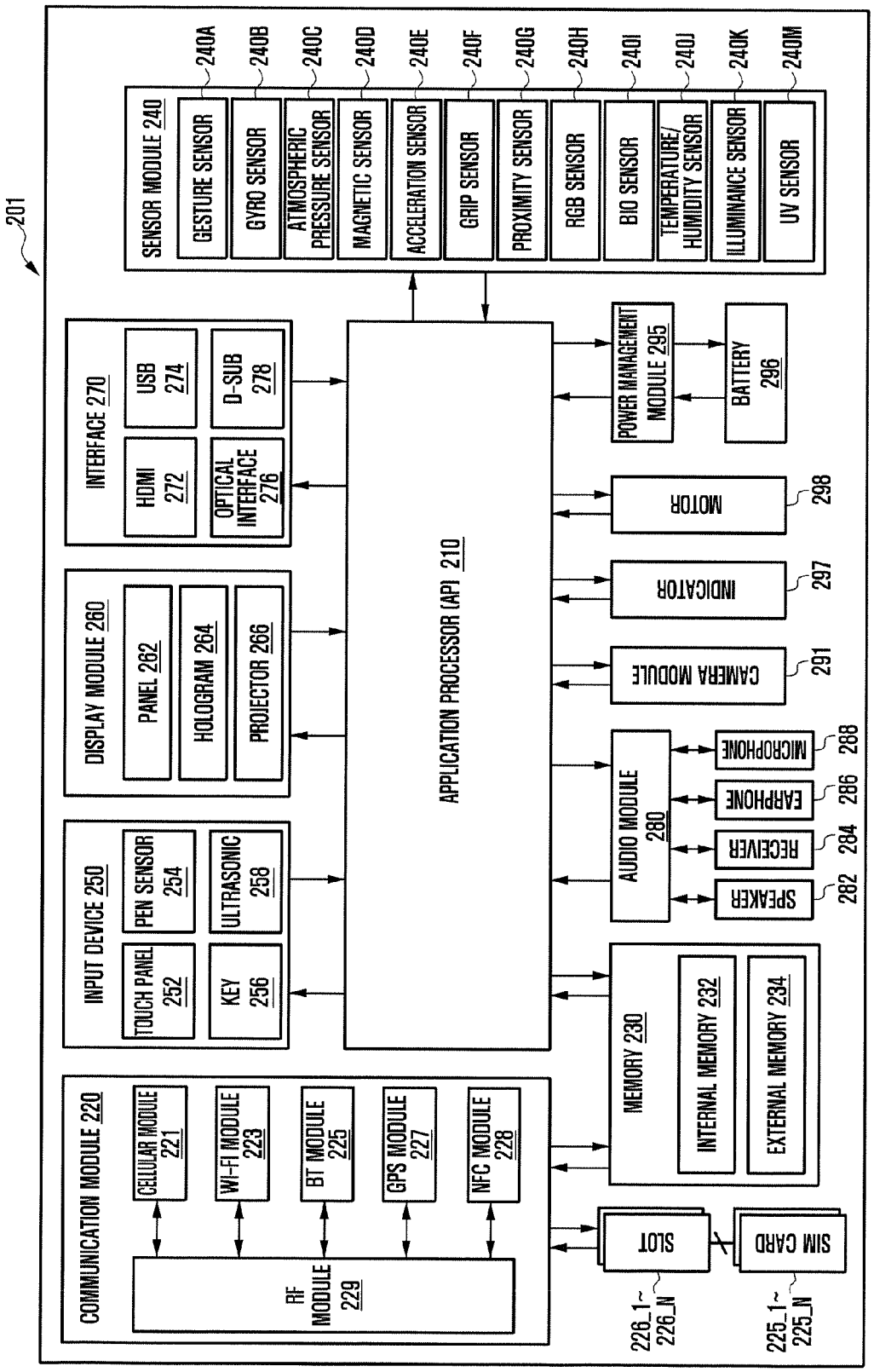
FIG. 2 is a block diagram of an electronic device according to embodiments of the present disclosure.

FIG. 2 illustrates a configuration of the electronic device according to embodiments of the present disclosure. The electronic device 201 can be of the whole or a part of the electronic device 101. The electronic device 201 includes an Application Processor (AP) 210, a communication module 220, a Subscriber Identity Module (SIM) card 224, a memory 230, a sensor module 240, an input device 250, a display 260, an interface 270, an audio module 280, a camera module 291, a power management module 295, a battery 296, an indicator 297, and a motor 298.

The AP 210 operates an Operating System (OS), application programs, or both, to control a plurality of hardware, software components, or a combination thereof, connected to the AP 210 and performs data-processing and operations on multimedia data. For example, the AP 210 can be implemented in the form of System on Chip (SoC). According to an embodiment, the AP 210 includes a Graphic Processing Unit (GPU) (not shown).

The communication module 220 (for example communication interface 160) performs data communication with other electronic devices (for example electronic device 104 and server 106) through a network. According to certain embodiments, the communication module 220 includes a cellular module 221, a Wi-Fi module 223, a BT module 225, a GPS module 227, an NFC module 228, and a Radio Frequency (RF) module 229.

The cellular module 221 is responsible for voice and video communication, text messaging, and Internet access services through a communication network, such as LTE, LTE-A, CDMA, WCDMA, UMTS, WiBro, and GSM networks. The cellular module 221 performs identification and authentication of electronic devices in the communication network using the SIM card 224. According to certain embodiments, the cellular module 221 performs at least one of the functions of the AP 210. For example, the cellular module 221 can perform at least a part of the multimedia control function.

According to certain embodiments, the cellular module 221 includes a Communication Processor (CP). The cellular module 221 can be implemented in the form of SOC. Although the cellular module 221 (for example communication processor), the memory 230, and the power management module 295 are depicted as independent components separated from the AP 210, the present disclosure is not limited thereto but can be embodied in a way that the AP includes at least one of the components (for example cellular module 221).

According to certain embodiments, each of the AP 210 and the cellular module 221 (for example communication processor) loads a command or data received from at least one of the components on a non-volatile or volatile memory and process the command or data. The AP 210 or the cellular module 221 can store the data received from other components or generated by at least one of other components in the non-volatile memory.

Each of the Wi-Fi module 223, the BT module 225, the GPS module 227, and the NFC module 228 includes a processor for processing the data it transmits or receives. Although the cellular module 221, the Wi-Fi module 223, the BT module 225, the GPS module 227, and the NFC module 228 are depicted as independent blocks; at least two of them (for example communication processor corresponding to the cellular module 221 and Wi-Fi processor corresponding to the Wi-Fi module 223) can be integrated in the form of SoC.

The RF module 229 is responsible for data communication, for example transmitting/receiving RF signals. Although not depicted, the RF module 229 can include a transceiver, a Power Amp Module (PAM), a frequency filter, and a Low Noise Amplifier (LNA). The RF module 229 also can include the elements for transmitting or receiving, or both, electric wave in free space, for example conductor or conductive wire. Although FIG. 2 is directed to the case where the Wi-Fi module 223, the BT module 225, the GPS module 227, and the NFC module 228 are sharing the RF module 229, the present disclosure is not limited thereto but can be embodied in a way that at least one of the Wi-Fi module 223, the BT module 225, the GPS module 227, and the NFC module 228 transmits/receives RF signals an independent RF module.

The SIM card 224 can be designed so as to be inserted into a slot formed at a predetermined position, such as a slot 226 of the electronic device. The SIM card 224 can store unique identity information, such as for example Integrated Circuit Card Identifier (ICCID) or subscriber information, such as an International Mobile Subscriber Identity (IMSI).

The memory 230, which can be the same as memory 130 includes at least one of the internal memory 232 and an external memory 234. The internal memory 232 includes at least one of a volatile memory, such as Dynamic Random Access Memory (DRAM), Static RAM (SRAM), Synchronous Dynamic RAM (SDRAM) or a non-volatile memory, One Time Programmable Read Only Memory (OTPROM), Programmable ROM (PROM), Erasable and Programmable ROM (EPROM), Electrically Erasable and Programmable ROM (EEPROM), mask ROM, flash ROM, NAND flash memory, and NOR flash memory.

According to certain embodiments, the internal memory 232 is a Solid State Drive (SSD). The external memory 234 can be a flash drive such as Compact Flash (CF), Secure Digital (SD), micro-SD, Mini-SD, extreme Digital (xD), and Memory Stick. The external memory 234 can be connected to the electronic device 201 through various interfaces functionally. According to certain embodiments, the electronic device 201 includes a storage device (or storage medium) such as hard drive.

The sensor module 240 measures physical quantity or checks the operation status of the electronic device 201 and converts the measured or checked information to an electric signal. The sensor module 240 can include at least one of gesture sensor 240A, Gyro sensor 240B, barometric sensor 240C, magnetic sensor 240D, acceleration sensor 240E, grip sensor 240F, proximity sensor 240G, color sensor 240H, such as Red, Green, Blue (RGB) sensor, bio sensor 240I, temperature/humidity sensor 240J, illuminance sensor 240K, and Ultra Violet (UV) sensor 240M. Additionally or alternatively, the sensor module 240 can include E-nose sensor (not shown), Electromyography (EMG) sensor (not shown), Electroencephalogram (EEG) sensor (not shown), Electrocardiogram (ECG) sensor (not shown), Infrared (IR) sensor (not shown), iris sensor (not shown), and fingerprint sensor (not shown). The sensor module 240 can further include a control circuit for controlling at least one of the sensors included therein.

The input device 250 includes a touch panel 252, a (digital) pen sensor 254, keys 256, and an ultrasonic input device 258. The touch panel 252 can be one of capacitive, resistive, infrared, microwave type touch panel. The touch panel 252 can include a control circuit. In the case of the capacitive type touch panel, it is possible to detect physical contact or approximation. The touch panel 252 can further include a tactile layer. In this case, the touch panel 252 can provide the user with haptic reaction.

The (digital) pen sensor 254 can be implemented with a sheet with the same or similar way as touch input of the user or a separate recognition sheet. The keys 256 can include physical buttons, optical key, and keypad. The ultrasonic input device 258 is a device capable of checking data by detecting sound wave through a microphone 288 and can be implemented for wireless recognition. According to certain embodiments, the electronic device 201 receives the user input made by means of an external device (for example computer or server) connected through the communication module 220.

The display 260, which can be the same as display module 150 can include a panel 262, a hologram device 264, and a projector 266. The panel 262 can be a Liquid Crystal Display (LCD) panel or an Active Matrix Organic Light Emitting Diodes (AMOLED) panel. The panel 262 can be implemented so as to be flexible, transparent, and/or wearable. The panel 262 can be implemented as a module integrated with the touch panel 252. The hologram device 264 can present 3-dimensional image in the air using interference of light. The projector 266 can project an image to a screen. The screen can be placed inside or outside the electronic device. According to certain embodiments, the display 260 includes a control circuit for controlling the panel 262, the hologram device 264, and the projector 266.

The interface 270 can include a High-Definition Multimedia Interface (HDMI) 272, a Universal Serial Bus (USB) 274, an optical interface 276, and a DOsubminiature (D-sub) 278. The interface 270 can include the communication interface 160 as shown in FIG. 1. Additionally or alternatively, the interface 270 can include a Mobile High-definition Link (MHL) interface, a SD/MMC card interface, and infrared Data Association (irDA) standard interface.

The audio module 280 converts sound to electric signal and vice versa. At least a part of the audio module 280 can be included in the input/output interface 140 as shown in FIG. 1. The audio module 280 processes the audio information input or output through the speaker 282, the receiver 284, the earphone 286, and the microphone 288.

The camera module 291 is a device capable of taking still and motion pictures and, according to an embodiment, includes at least one image sensor (for example front and rear sensors), a lens (not shown), and Image Signal Processor (ISP) (not shown), and a flash (for example LED or xenon lamp) (not shown).

The power management module 295 manages the power of the electronic device 201. Although not shown, the power management module 295 can include a Power Management Integrated Circuit (PMIC), a charger Integrated Circuit (IC), a battery, and a battery or fuel gauge.

The PMIC can be integrated into an integrated circuit or SoC semiconductor. The charging can be classified into wireless charging and wired charge. The charger IC can charge the battery and protect the charger against overvoltage or overcurrent. According to certain embodiments, the charger IC includes at least one of wired charger and wireless charger ICs. Examples of the wireless charging technology includes resonance wireless charging and electromagnetic wave wireless charging, and there is a need of extra circuit for wireless charging such as coil loop, resonance circuit, and diode.

The battery gauge measures the residual power of the battery 296, charging voltage, current, and temperature. The battery 296 stores or generates power and supplies the stored or generated power to the electronic device 201. The battery 296 can include a rechargeable battery or a solar battery.

The indicator 297 displays operation status of the electronic device 201 or a part of the electronic device, booting status, messaging status, and charging status. The motor 298 converts the electronic signal to mechanical vibration. Although not shown, the electronic device 201 includes a processing unit (for example GPU) for supporting mobile TV. The processing unit for supporting the mobile TV is able to process the media data abiding by the broadcast standards such Digital Multimedia Broadcasting (DMB), Digital Video Broadcasting (DVB), and media flow.

As described above, the electronic device operating method and apparatus of the present disclosure is capable of providing diverse screen displays in adaptation to various conditions to implement optimal environment for utilizing the electronic device, resulting in improvement of user convenience. Also, the electronic device operating method and apparatus of the present disclosure is advantageous in terms of facilitating navigation between folders by sorting the folders by hierarchical level.

The above enumerated components of the electronic device of the present disclosure can be implemented into one or more parts, and the names of the corresponding components can be changed depending on the kind of the electronic device. The electronic device of the present disclosure can include at least one of the aforementioned components with omission or addition of some components. The components of the electronic device of the present disclosure can be combined selectively into an entity to perform the functions of the components equally as before the combination.

The term "module" according to the embodiments of the disclosure, means, but is not limited to, a unit of one of software, hardware, and firmware or any combination thereof. The term "module" can be used interchangeably with the terms "unit," "logic," "logical block," "component," or "circuit." The term "module" can denote a smallest unit of component or a part thereof. The term "module" can be the smallest unit of performing at least one function or a part thereof. A module can be implemented mechanically or electronically. For example, a module can include at least one of Application-Specific Integrated Circuit (ASIC) chip, Field-Programmable Gate Arrays (FPGAs), and Programmable-Logic Device known or to be developed for certain operations.

Figure 3:
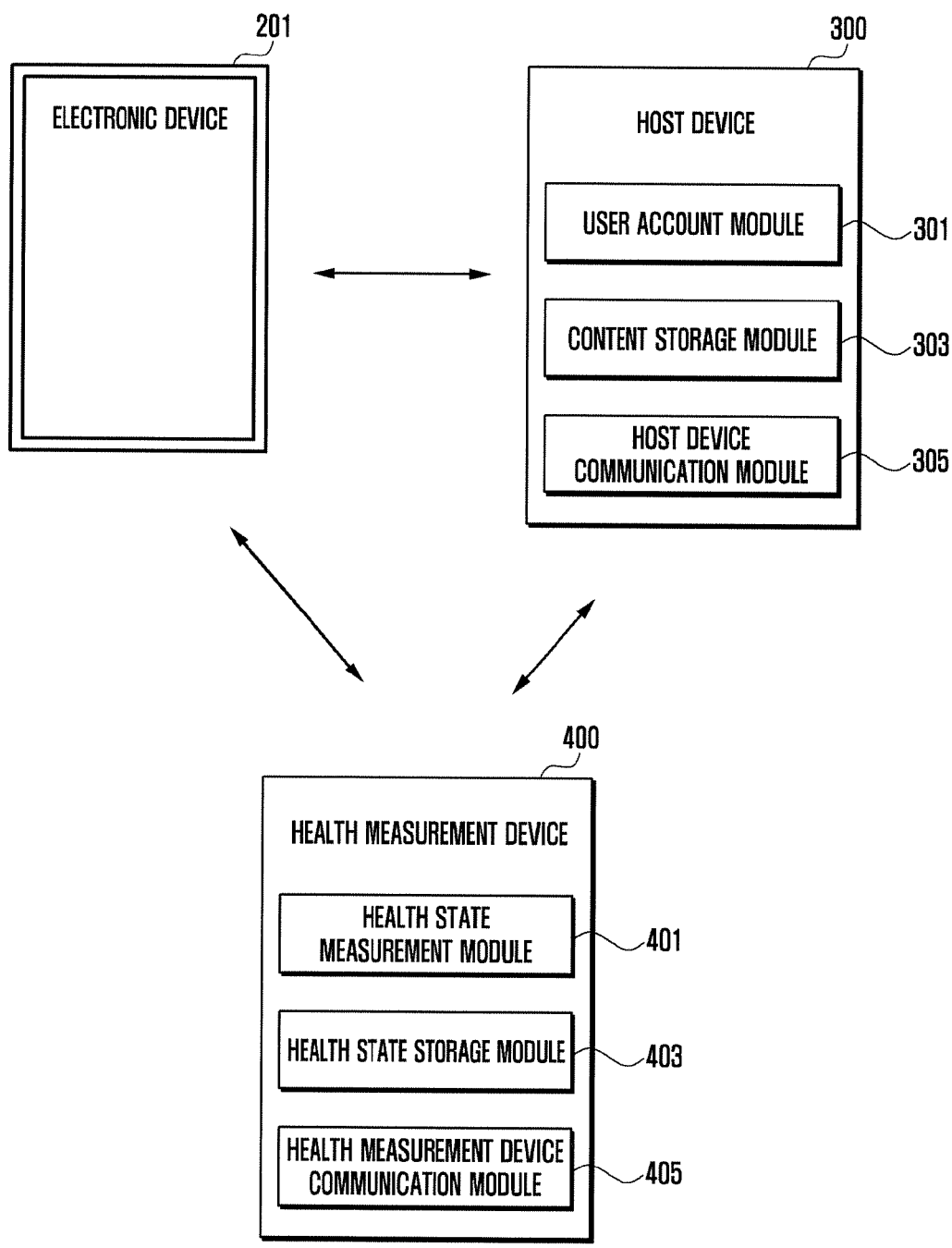
FIG. 3 illustrates a network environment including an electronic device according to embodiments of the present disclosure.

FIG. 3 illustrates a network environment including an electronic device 201 according to embodiments of the present disclosure.

According to certain embodiments of the present disclosure, the electronic device 201, a host device 300, and a health measurement device 400 constructs a network environment there between. The electronic device 201 can include the electronic device illustrated in FIGS. 1 and 2, and the AP 210 can be exchanged with the term such as a control module or a process which can control the electronic device.

The host device 300 according to embodiment of the present disclosure includes at least one module of a user account module 301, a content storage module 303, and a host device communication module 305.

According to embodiments of the present disclosure, the user account module 301 stores information on a user account of the electronic device 201. The information on the user account can be at least one of a name, nickname, password, and address of the user who activates an application 500 by using the electronic device 201, and an identification number of the electronic device 201. For example, the user can activate the application 500 of the electronic device 201 to input a name, IDentification (ID), and password of the user. The input name and ID of the user can be transmitted to the host device 300 through the communication module 220. The user account module 301 can store health information related to the received user account.

According to embodiments of the present disclosure, the content storage module 303 stores basic health data corresponding to the user account. For example, the user can activate the application 500 to input and store information related to gender, height, and weight of the user, and a health index (body fat rate or information on whether the user is admitted to a hospital or not) recognized in advance by the user as additional elements of the user account. The input and storage of the information can include an operation in which the user touches and inputs information related to the user account into the display module 260 and then transmits the touched and input information related to the user account to the host device 300. Accordingly, the content storage module 303 can store the received related information.

Further, according to embodiments of the present disclosure, the host device 300 analyzes pieces of basic health data corresponding to user accounts stored in the content storage module 303 and classify a predetermined user account as one similar group account among a plurality of similar group accounts. In addition, according to embodiments of the present disclosure, the host device 300 determines similar group accounts based on at least one piece of basic health data of the user account and health state measurement data of the user account.

According to embodiments of the present disclosure, the host device 300 classifies pieces of basic health data of the user accounts subscribed to the application 500 into several similar groups based on a preset reference. For example, the host device 300 classifies the user accounts based on at least one reference among gender, height, weight, body fat rate, muscle amount, and recommended calorie intake and determine a similar group.

More specifically, for example, ten user accounts are stored in the content storage module 303. When recommended calorie intakes among the pieces of basic health data of six user accounts are similar to each other (for example, when, based on the recommended calorie intake of one user account, recommended calorie intakes of other user accounts are within an error range of +−5%), the host device 300 determines that the six user accounts having similar recommended calorie intakes are first similar group accounts and the four remaining user accounts are second similar group accounts.

According to embodiments of the present disclosure, when the host device 300 receives basic health data or health measurement data corresponding to the user account, the host device 300 determines a similar group account which includes the received basic health data or health measurement data and decides the similar group account of the received user account.

Further, the host device communication module 305 is a module that can communicate with the electronic device 201 and the health measurement device communication unit 405. The host device communication module 305 can activate the application 500 and thus the electronic device 201 can receive a request signal making a request for pieces of health state measurement data of similar group accounts. The host device communication module 305 can transmit the pieces of health state measurement data of the similar group accounts stored in the content storage unit 303 in response to the request signal.

Further, according to another embodiment of the present disclosure, the host device communication module 305 receives pieces of health measurement data corresponding to the user accounts from the health measurement device 400. The host device 300 stores the received pieces of health measurement data in the content storage module 303. At this time, the host device 300 can store pieces of pre-stored health measurement data corresponding to the user account. For example, when the host device 300 receives health measurement data of the user account, the host device 300 can identify the user account and make a control to store the health measurement data of the user account.

According to an embodiment of the present disclosure, the health measurement device 400 includes at least one of a health state module 401, a health state storage module 403, and a health measurement device communication module 405.

According to an embodiment of the present disclosure, the health measurement device 400 includes a blood pressure measuring device, a pulse measuring device, a momentum measuring device, a skin current measuring device, a body temperature measuring device, and a pedometer. Further, the health measurement device 400 can include a wearable health measurement device. The health measurement device 400 can include, for example, a momentum measuring device, a shoe sensor, a wrist band, Google glass, a smart watch, Galaxy Gear, and a fuel band.

Further, according to an embodiment of the present disclosure, when the user measures health-related information by using the health measurement device 400, the health state storage module 403 stores information related to the health-related information. For example, when the user measures their body temperature by using the health measurement device 400 including a body temperature measuring device, the health state storage module 403 can store the measured body temperature.

The health measurement device communication module 405 can communicate with the electronic device 200 and the host device module 300. According to an embodiment of the present disclosure, after activating the application 500, the user of the electronic device 200 measures health using the health measurement device 400. When receiving a request signal related to the health measurement, the health measurement device communication module 405 can transmit health measurement information to the electronic device 200 or the host device 300.

Further, according to an embodiment of the present disclosure, the health measurement device communication module 405 uses short-range technologies, such as Bluetooth, Radio Frequency IDentification (RFID), Infrared Data Association (IrDA), Ultra WideBand (UWB), ZigBee and the like. More specifically, the health measurement device communication module 405 can be used when the health measurement device 400 transmits the measured data to the electronic device 200.

Further, according to an embodiment of the present disclosure, the health measurement device communication module 405 transmits the data measured by the health measurement device 400 to the electronic device 200 using wireless Internet access (for example, Wireless Local Area Network (WLAN), Wi-Fi, Wireless broadband (Wibro), World Interoperability for Microwave Access (Wimax), or High Speed Downlink Packet Access (HSPDA).

FIGS. 4 to 7 illustrate user interfaces related to the application 500 of the electronic device 201.

According to an embodiment of the present disclosure, as the display module 260 receives a touch input event, the AP 210 activates the application 500. The display module 260 can display the activated application 500.

Figure 4:
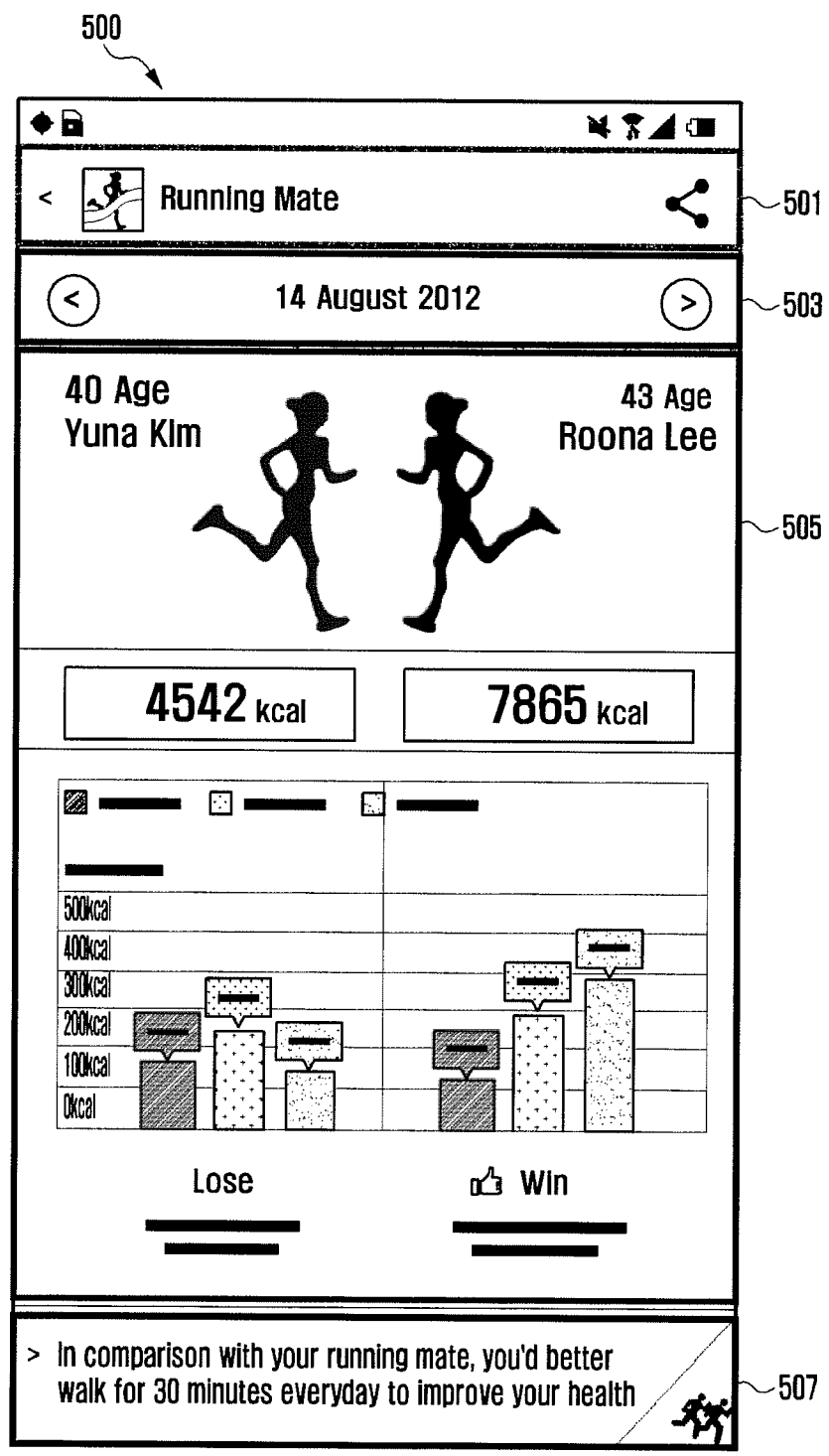
FIGS. 4, 5, 6 and 7 illustrate user interfaces related to an application of an electronic device according to embodiments of the present disclosure.

According to an embodiment of the present disclosure, the display module 260 displays a title display area 501, a date display area 503, an exercise state display area 505, and a reference display area 507 as illustrated in FIG. 4.

According to an embodiment of the present disclosure, the title display area 501 displayed by the display module 260 includes a user interface related to the title displayed by the application 500. For example, the display module 260 can display a user interface such as a "Running Mate" as illustrated in FIG. 4. When the display module 260 receives a touch input event for changing the title display area 501, the AP 210 can change the user interface corresponding to the received touch input event. Further, as the title display area 501 changes, the user interface related to the application 500 displayed by the display module 260 can be changed.

According to an embodiment of the present disclosure, the date display area 503 displayed by the display module 260 includes a user interface related to the year, month, and day. For example, the display module 260 can display a user interface such as a "14 Aug. 2012" in the date display area 503. The date display area 503 displayed by the display module 260 can be changed according to a user's intention. Further, the AP 210 can display, via display module 260, a current date by default. In addition, when the display module 260 receives a touch input event for changing the date in the date display area 503, the AP 210 can change the user interface displayed in the date display area 503 and display a user interface corresponding to the changed date in the exercise state display area 505 and the reference display area 507.

According to an embodiment of the present disclosure, the display module 260 displays, in the health state display area 505, data related to a name, nickname, gender, weight, and burnt calories of the user account, data related to a name, nickname, gender, weight, and burnt calories of an account to be compared with the user account, and the user interface. Further, the display module 260 can display, in the health state display area 505, a user interface for comparing calorie data, muscle amount data, and body fat data between the user account and the account to be compared with the user account during a predetermined period of the user account.

For example, according to an embodiment of the present disclosure, the display module 260 displays, in the exercise state display area 505, a user interface corresponding to the user account and a user interface corresponding to the account with which to be compared, with at least one of different colors, sizes, and images.

Further, according to an embodiment of the present disclosure, the display module 260 displays, in the health state display area 505, burnt calories of the user account received from the health measurement device 400 and burnt calories of the account to be compared with the user account. According to an embodiment of the present disclosure, the display module 260 displays, in the health state display area 505, burnt calories of the user account measured using a sensor (for example, a body heat measurement sensor, a pedometer, or a heartbeat sensor) mounted to the electronic device 200.

According to an embodiment of the present disclosure, the AP 210 calculates recommended calorie data by using age data, height data, weight data, muscle amount data, and body fat data of the user account. A method of calculating the recommended calorie data can be determined by a predetermined equation, or an equation downloaded through a health-related link. For example, when recommended calorie data pre-stored in the electronic device 201 has data corresponding to a man who is 20-29 years old, 67 Kg, and 174 cm tall, recommended calorie data can be set as 2500 Kcal. When a recommended calorie data pre-stored in the electronic device 201 has data corresponding to a man who 30-49 years old, 63 Kg, and 170 cm tall, recommended calorie data can be set as 2500 Kcal.

According to an embodiment of the present disclosure, the display module 260 displays, in the health state display area 505, a user interface for comparing result values of the pieces of health state measurement data of the user account and the account to be compared with the user account. For example, the display module 260 can display, in the health state display area 505, a user interface for comparing the pieces of health state measurement data (for example, burnt calorie data or body fat data) of the user account and the account to be compared with the user account. More specifically, for example, as illustrated in FIG. 4, when the result values of the burnt calorie data and the body fat data of the account to be compared with the user account are larger than the result values of the burnt calorie data and the body fat data of the user account, the display module 260 can display a "Lose" user interface on a side of the health state display area corresponding to the user interface and display a "Win" user interface on a side of the health state display area corresponding to the account to be compared with the user account.

Further, according to an embodiment of the present disclosure, the display module 260 displays, in the reference display area 507, a reference comment related to a health state. The AP 210 can compare and analyze pieces of data to determine one comment from the pre-stored health comments and can control the display module 260 to display the one comment. The pre-stored health comments can refer health comments stored based on recommended calories, burnt calories, or weight.

For example, a health comment of a first group which weighs 10 Kg more than a recommended weight can be pre-stored in the memory 230 as "run for 1 hour everyday", and a health comment of a second group which weighs 5 Kg~10 Kg less than a recommended weight can be pre-stored in the memory 230 as "run for 30 minutes or more everyday". The AP 210 can extract one health comment from the pre-stored health comments and make a control to display the extracted health commend by mapping the health comments and the pieces of health measurement data of the user account. More specifically, for example, the display module 260 can display "In comparison with your running mate, you'd better walk for 30 minutes every day to improve your health" in the reference display area 507 as illustrated in FIG. 4.

Figure 5:
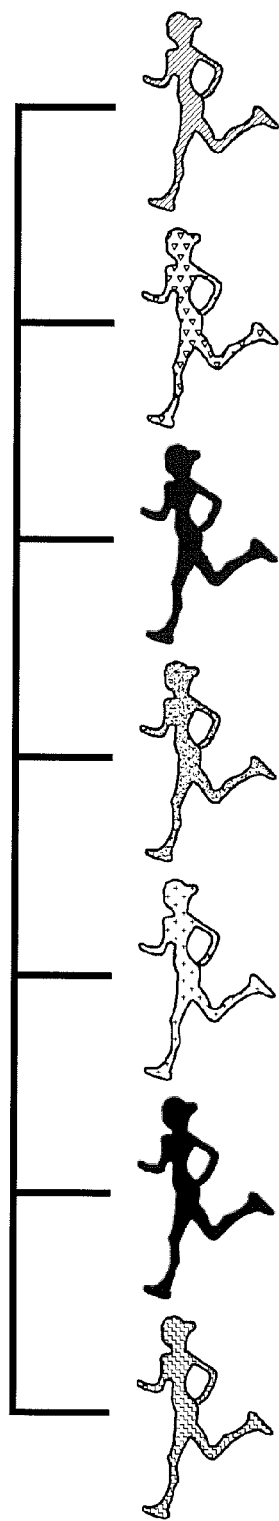

According to an embodiment of the present disclosure, the display module 260 displays a user interface related to similar group accounts as illustrated in FIG. 5. The similar group accounts can be determined based on at least one piece of the pre-stored basic health data of the user account and health state measurement data of the user account.

Further, the display module 260 can display user interfaces corresponding to the similar group accounts, a user interface corresponding to the user account, and a user interface corresponding to the account to be compared with the user account, with at least one of different colors, sizes, and images.

For example, the display module 260 can display the user interface corresponding to the user account with a red color, the user interface corresponding to the account to be compared with the user interface with a blue color, and the user interfaces corresponding to other similar group accounts with green and blue colors.

Figure 6:
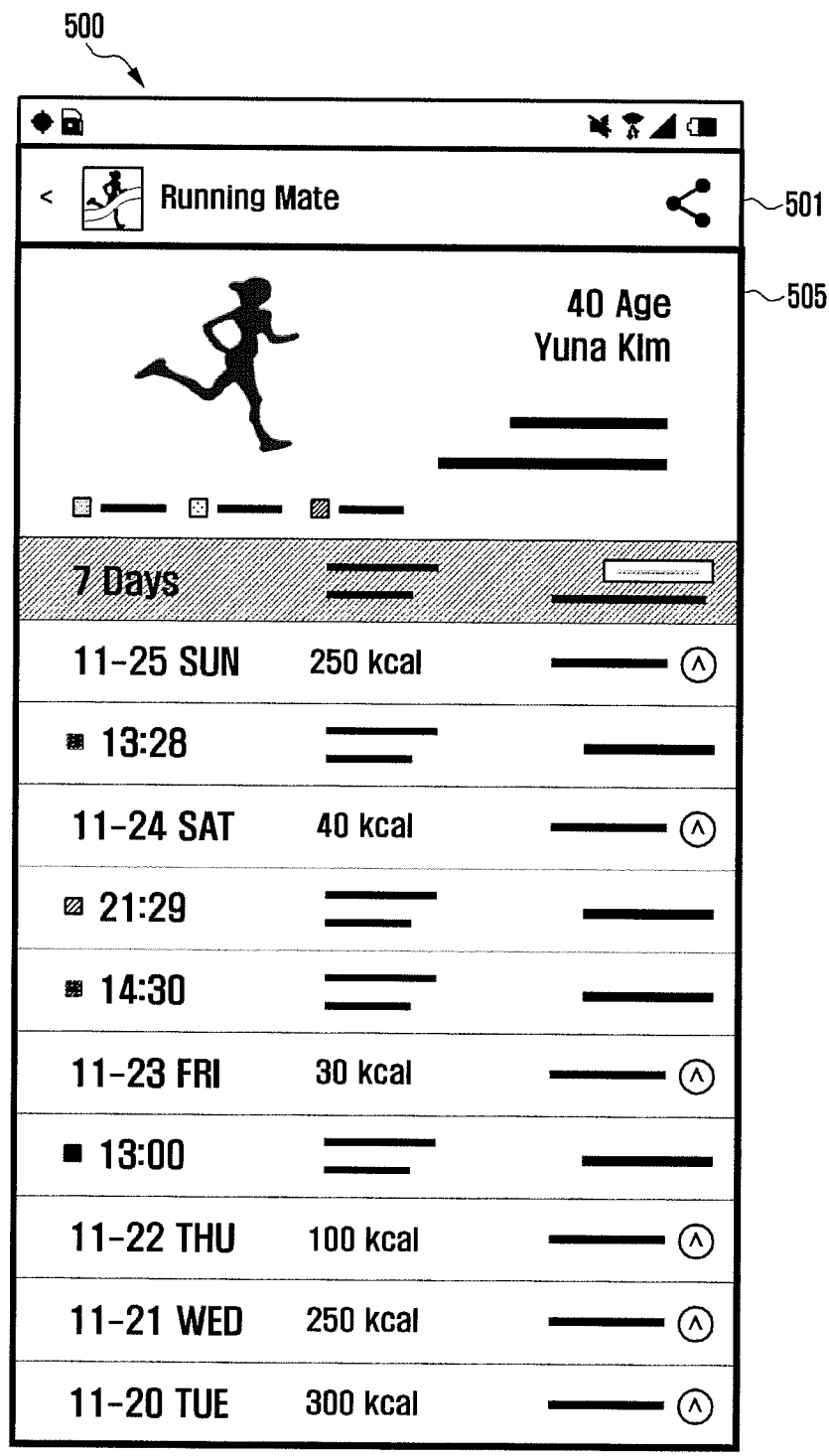

According to an embodiment of the present disclosure, the display module 260 displays the title display area 501 and the health state display area 505 as illustrated in FIG. 6.

The title display area 501 displayed by the display module 260 can include a user interface related to the title displayed by the application 500. When the display module 260 receives a touch input event for changing the title display area 501, the AP 210 can change the user interface corresponding to the received touch input event. Further, as the title display area 501 is changed, the user interface related to the application 500 displayed by the display module 260 can be changed.

According to an embodiment of the present disclosure, the health state display area 505 displayed by the display module 260 includes a schedule table of the user account. For example, as illustrated in FIG. 6, the display module 260 can display health measurement data based on each date with respect to the selected user account.

For example, the display module 260 can display a user interface related to a result value of burnt calories such as 2014/01/02: 300 Kcal burned, 2014/01/03: 130 Kcal burned, and 2014/01/04: 140 Kcal burned.

Figure 7:
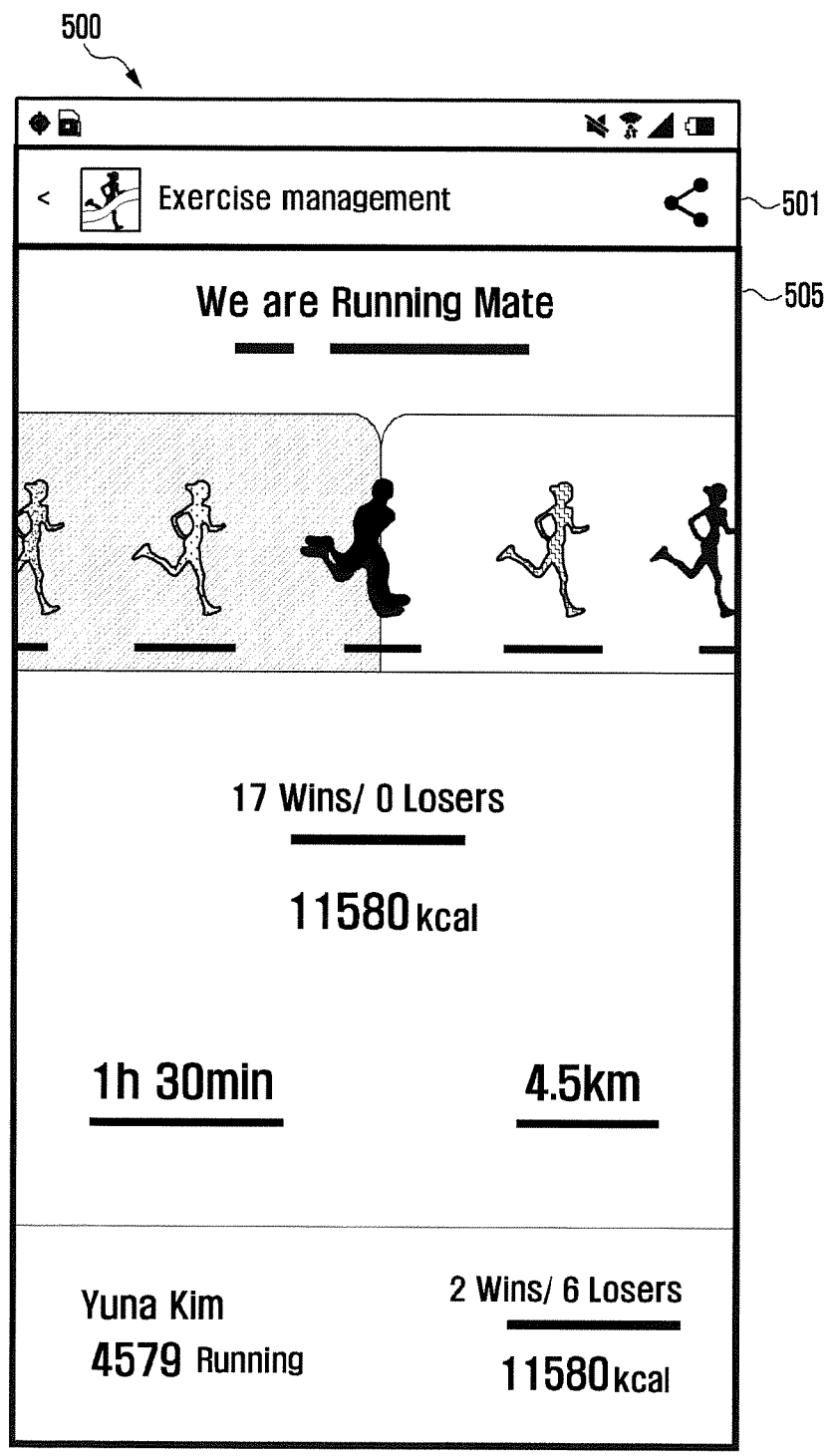

According to an embodiment of the present disclosure, the display module 260 can display the title display area 501 and the health state display area 505 as illustrated in FIG. 7.

The title display area 501 displayed by the display module 260 can include a user interface related to the title displayed by the application 500. When the display module 260 receives a touch input event for changing the title display area 501, the AP 210 can change the user interface corresponding to the received touch input event. Further, as the title display area 501 is changed, the user interface related to the application 500 displaying the display module 260 can be changed.

For example, according to an embodiment of the present disclosure, the display module 260 displays, in the exercise state display area 505, user interfaces corresponding to similar group accounts, a user interface corresponding to the user account, and a user interface corresponding to the account with which to be compared, with at least one of different colors, sizes, and images. For example, the display module 260 can display a first user interface with a black color, the user interface corresponding to the account with which to be compared, with a pink color, and the user interfaces corresponding to the similar group accounts with yellow and green colors.

Further, according to an embodiment of the present disclosure, the AP 210 compares health measurement data of the user account and health measurement data of the similar group accounts and determine ranks of the user accounts. For example, the display module 260 can compare pieces of health measurement data of the similar group accounts, so as to determine and display a top ranked user account and display ranks of the user accounts. The measurement data can be determined based on burnt calories, a body fat rate, or a goal achievement rate. For example, when the burnt calorie of the user account among ten similar group accounts is ranked third, the display module 260 can display a user interface corresponding to the user account as a "third place".

Further, according to an embodiment of the present disclosure, the display module 260 compares and displays health measurement data of a first user account and pieces of health measurement data of similar group accounts. For example, the display module 260 can display a body fat rate which is an example of the health measurement data of the user account and display body fat rates of similar group accounts. Further, the display module 260 can display a result value calculated according to a change in the body fat rate of each user account based on each date, each week, and each month.

Figure 8:
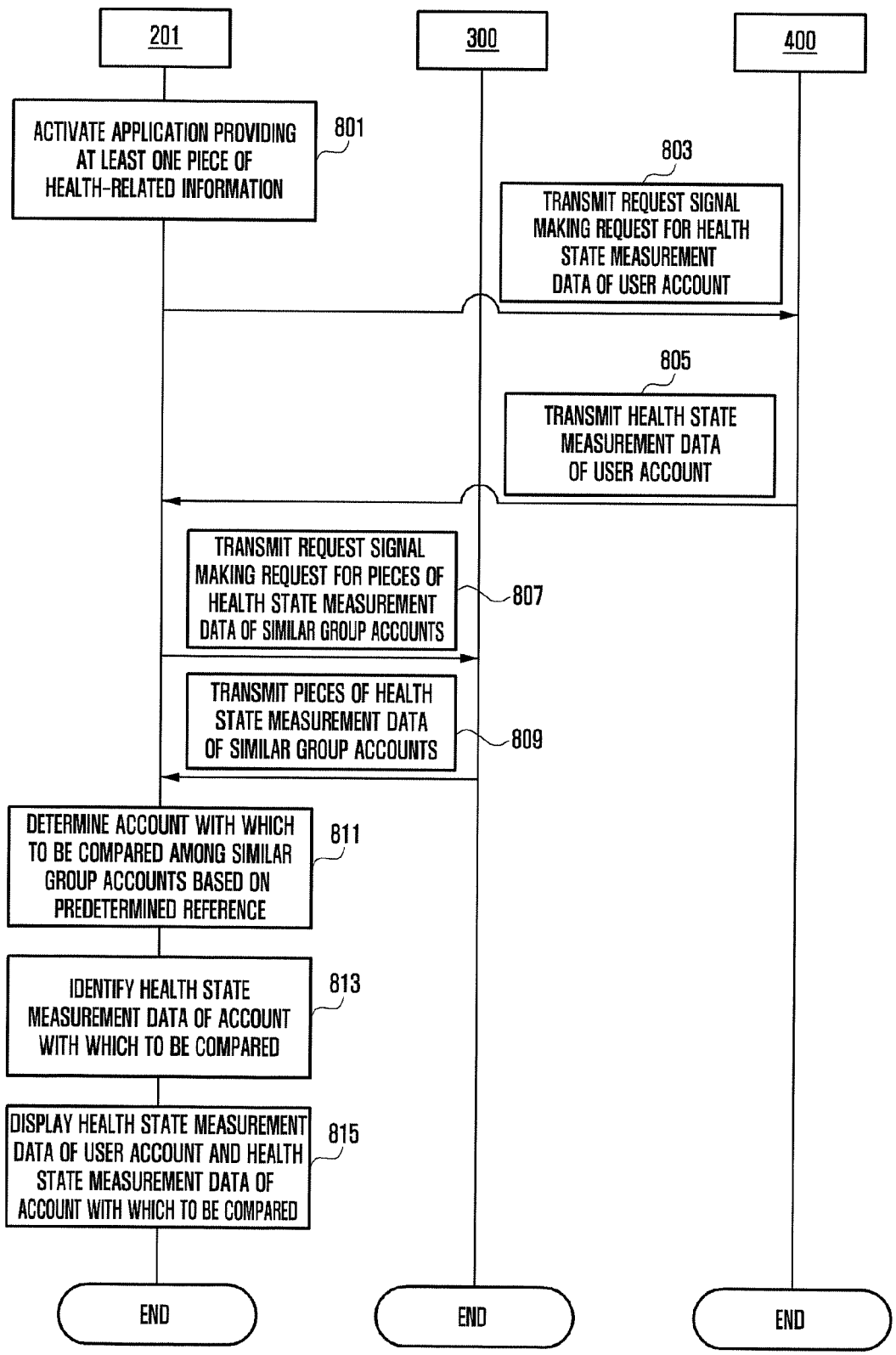
FIG. 8 is a flowchart of a network environment including an electronic device according to embodiments of the present disclosure.

FIG. 8 is a flowchart of a network environment including the electronic device 201. The electronic device 201 activates the application 500 providing at least one piece of health-related information in step 801. For example, when the user inputs a touch event for the application 500, the electronic device 201 can activate the application 500.

After the application 500 is activated, the AP 210 identifies the user account stored in the application 500. When the display module 260 receives a touch input event making a request for health measurement data of the user account, the AP 210 can control the communication module 200 to transmit a request signal making a request for health state measurement data of the user account in step 803. The request signal can include basic data (for example, a name, nickname, phone number, and IDentification (ID)) of the pre-stored user account.

When the health measurement device 400 receives a request signal of health state measurement data of the user account, the health measurement device 400 determines health measurement data (for example, a blood-sugar level, body temperature, and body fat rate corresponding to the user account) corresponding to the user account. The health measurement device 400 transmits health state measurement data of the user account to the electronic device 201 in step 805. The electronic device 200 receives and stores the health state measurement data of the user account transmitted by the health measurement device 400.

The electronic device 201 transmits a request signal making a request for health state measurement data of similar group accounts to the host device 300 in step 807. When the host device 300 receives the request signal from the electronic device 201, the host device 300 determines at least one piece of similar groups based on basic health data of the user account and health state measurement data of the user account. For example, different user accounts having the same gender and similar body fat rates (for example, when a difference between body fat rates is within +−5% or a difference between aimed calories is within +−10%) can be classified into a first similar group, a second group, and a third similar group.

Further, according to an embodiment of the present disclosure, the similar group accounts continuously change. The host device 300 transmits health state measurement data of the determined similar group accounts to the electronic device 200 in step 809. The electronic device 201 receives the health state measurement data of the similar group accounts from the host device 300.

The electronic device 201 determines an account with which to be compared from similar group accounts based on a predetermined reference in step 811. The account with which to be compared refers to a user account to compare to the user account of the application 500, and is not the user account of the application 500. Further, the account with which to be compared may continuously change and be updated among the similar group accounts. According to an embodiment of the present disclosure, the change and update of the similar group accounts and the account with which to be compared is pre-designated by the user or can be performed when the display module 260 receives a touch input event related to the change and update.

The electronic device 201 identifies health state measurement data of the account with which to be compared, in step 813. Further, in step 815, the display module 260 displays the health state measurement data of the user account and the health state measurement data of the account with which to be compared. The display module 260 displays a user interface corresponding to the user account and a user interface corresponding to the account with which to be compared, based on a result of comparison between the pieces of health state measurement data of the user account and the account with which to be compared.

The display module 260 displays the user interface corresponding to the user account and the user interface corresponding to the account with which to be compared, with at least one of different colors, sizes, and images.

According to an embodiment of the present disclosure, based on result values of health state measurement data included in the health state measurement data of the user account and the account with which to be compared, the display module 260 displays a user interface indicating which result value between the user account and the account with which to be compared has a higher value. For example, the display module 260 can display a "win" user interface when the health state measurement data of the user account has a higher value, and display a "lose" user interface when the health state measurement data of the account with which to be compared has a higher value.

Figure 9:
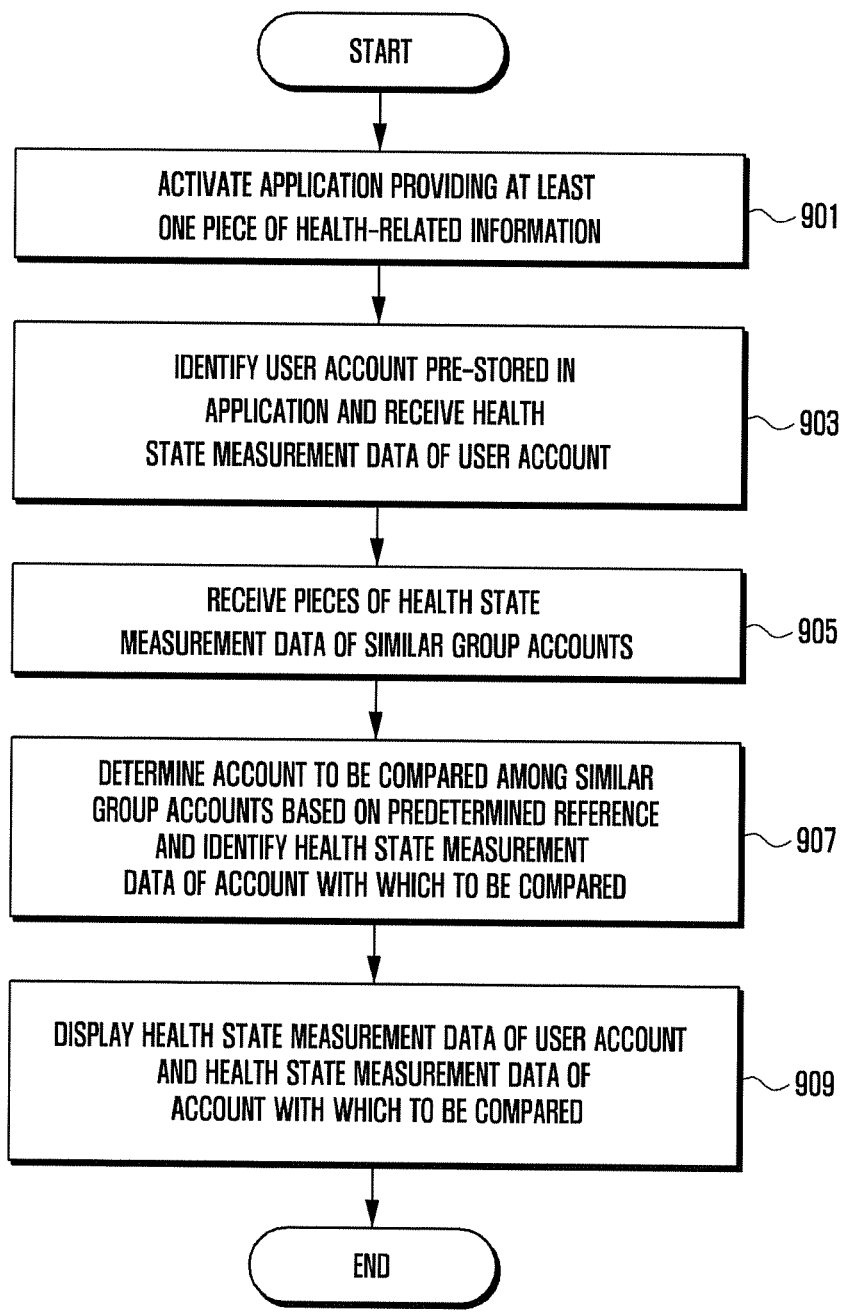
FIG. 9 is a flowchart illustrating a display of data related to an application of an electronic device according to embodiments of the present disclosure.

FIG. 9 is a flowchart illustrating a display of data related to the application 500 of the electronic device 201.

When the display module 260 receives a touch input event for activating the application 500, the AP 210 activates the application 500 which provides at least one piece of health-related information in step 901.

The AP 210 identifies a user account pre-stored in the application 500 and receives health state measurement data of the user account from the health measurement device 400 in step 903. The AP 210 can store the health state measurement data of the user account in the memory 230.

The communication module 220 receives health state measurement data of similar group accounts from the host device 300 in step 905. The AP 210 can store the received health state measurement data. Further, the AP 210 compares an account with which to be compared, from the similar group accounts based on a predetermined reference and identifies health state measurement data of the account with which to be compared, in step 907. The predetermined reference can be health measurement data (for example, burnt calories, gender, age, and height) set by the user. Further, the user can select one user account from the similar group accounts.

In step 909, the display module 260 displays the health state measurement data of the user account and the health state measurement data of the account with which to be compared. According to an embodiment of the present disclosure, the display module 260 displays, in the health state display area 505, user interfaces corresponding to similar group accounts, a user interface corresponding to the user account, and a user interface corresponding to the account with which to be compared, with at least one of different colors, sizes, and images.

Further, according to an embodiment of the present disclosure, the AP 210 compares health measurement data of the user account and health measurement data of the similar group accounts and determine classes of the user accounts. For example, the display module 260 can determine and display a first ranked user account among the similar group accounts, and can display ranks of the user accounts.

Figure 10:
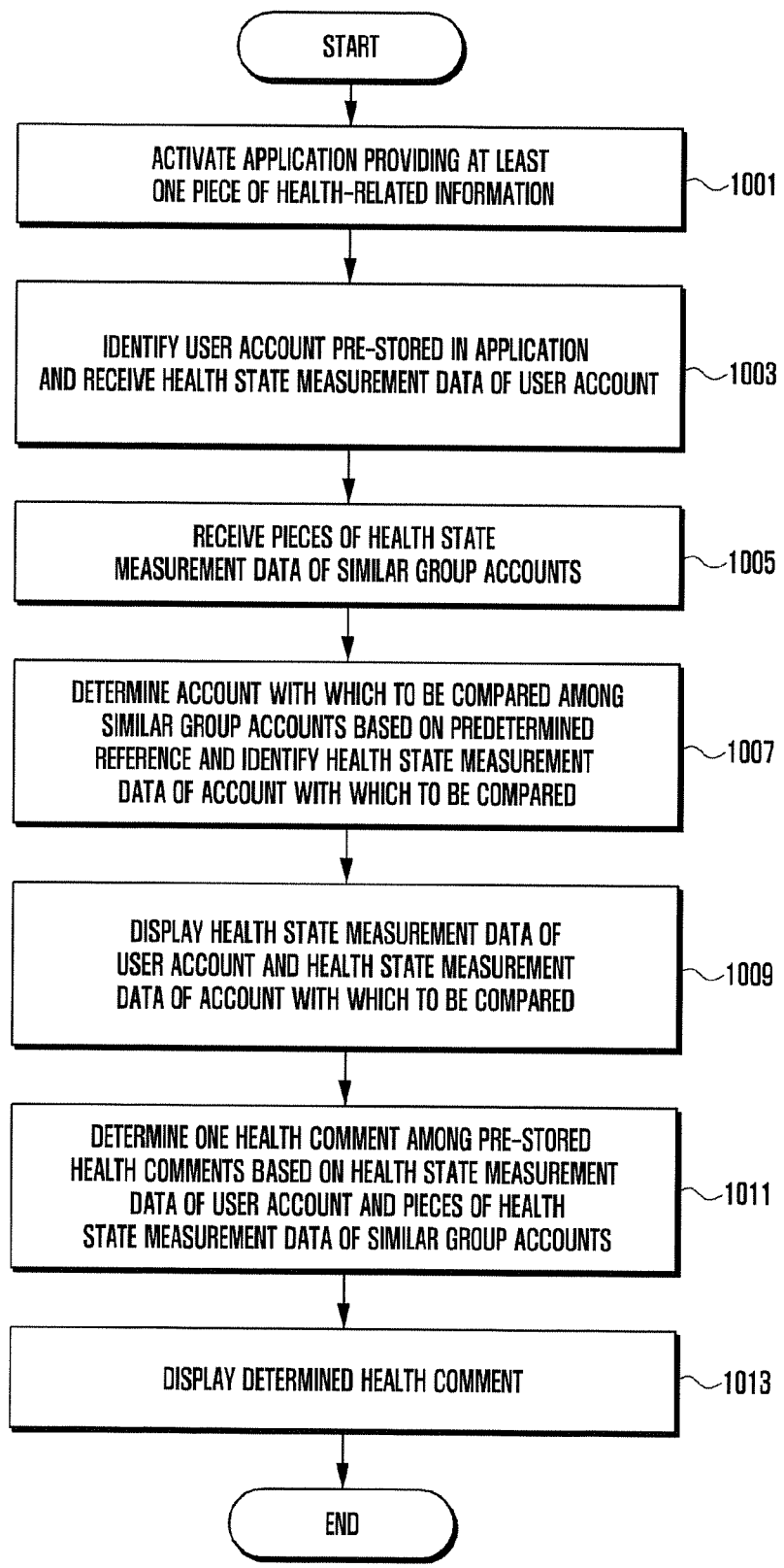
FIG. 10 is a flowchart illustrating a display of data related to an application of an electronic device.

FIG. 10 is a flowchart illustrating a display of data related to the application 500 of the electronic device 201.

When the display module 260 receives a touch input event for activating the application 500, the AP 210 activates the application 500 which provides at least one piece of health-related information in step 1001.

The AP 210 identifies a user account pre-stored in the application 500 and receives health state measurement data of the user account from the health measurement device 400 in step 1003. The AP 210 can store the health state measurement data of the user account in the memory 230.

The communication module 220 receives health state measurement data of similar group accounts from the host device 300 in step 1005. The AP 210 can store the received health state measurement data. Further, the AP 210 compares an account with which to be compared, from the similar group accounts based on a predetermined reference and identifies health state measurement data of the account with which to be compared, in step 1007. The predetermined reference can be health measurement data (for example, burnt calories, gender, age, and height) set by the user. Further, the user can select one user account from the similar group accounts.

In step 1009, the display module 260 displays the health state measurement data of the user account and the health state measurement data of the account with which to be compared. According to an embodiment of the present disclosure, the display module 260 displays, in the health state display area 505, user interfaces corresponding to similar group accounts, a user interface corresponding to the user account, and a user interface corresponding to the account with which to be compared, with at least one of different colors, sizes, and images.

Further, according to an embodiment of the present disclosure, the AP 210 compares health measurement data of the user account and health measurement data of the similar group accounts and determine ranks of the user accounts. For example, the display module 260 can determine and display a first ranked user account among the similar group accounts, and can display ranks of the user accounts.

Subsequently, the AP 210 determines one health comment among the pre-stored health comments based on the health state measurement data of the user account and the health state measurement data of the similar group accounts in step 1011. The pre-stored health comments can refer health comments stored based on recommended calories, burnt calories, or weight.

Subsequently, the display module 260 displays the determined health commend in step 1013. For example, a first health comment is mapped when a body fat rate is larger than or equal to 10%, and a second health commend is mapped when a body fat rate is larger than or equal to 5% and smaller than 10%. When a body fat rate of the user account is 7%, the AP 210 can control the display module 260 to display the second health comment in step 1013.

Figure 11:
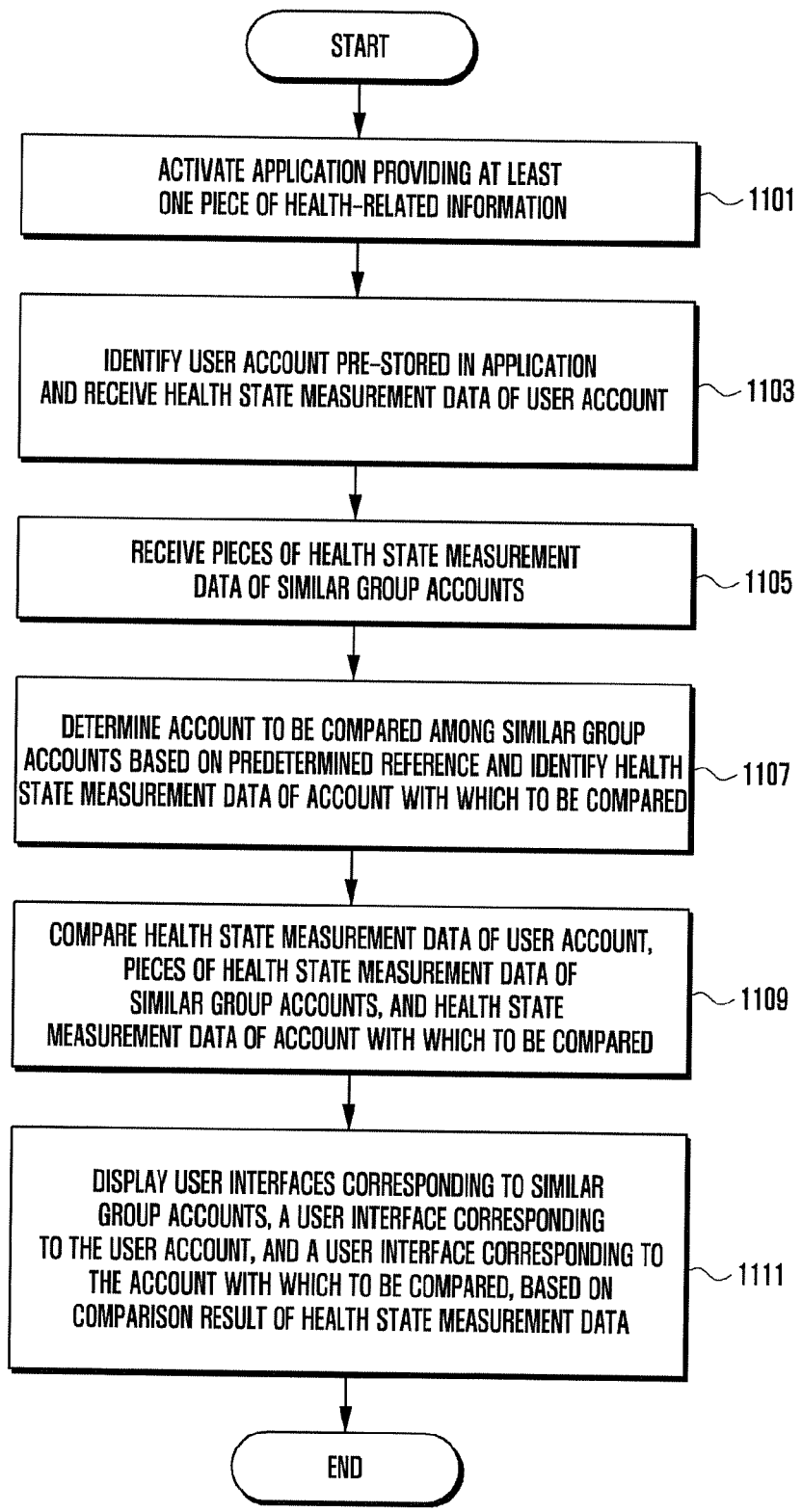
FIG. 11 is a flowchart illustrating a display of data related to an application of an electronic device according to embodiments of the present disclosure.

FIG. 11 is a flowchart illustrating a display of data related to the application 500 of the electronic device 201.

When the display module 260 receives a touch input event for activating the application 500, the AP 210 activates the application 500 which provides at least one piece of health-related information in step 1101.

The AP 210 identifies a user account pre-stored in the application 500 and receives health state measurement data of the user account from the health measurement device 400 in step 1103. The AP 210 can store the health state measurement data of the user account in the memory 230.

The communication module 220 receives health state measurement data of similar group accounts from the host device 300 in step 1105. The AP 210 can store the received health state measurement data. Further, the AP 210 compares an account with which to be compared, from the similar group accounts based on a predetermined reference and identifies health state measurement data of the account with which to be compared, in step 1107. The predetermined reference can be health measurement data (for example, burnt calories, gender, age, and height) set by the user. Further, the user can select one user account from the similar group accounts.

The AP 210 compare health state measurement data of the user account, health state measurement data of similar group accounts, and health state measurement data of the account with which to be compared, in step 1109. The health state measurement data of each user account can include body fat data and burnt calorie data.

The display module 260 can display a user interface corresponding to the similar group accounts, a user interface corresponding to the user account, and a user interface corresponding to the account with which to be compared, based on a result of the comparison between the pieces of health state measurement data in step 1111.

According to an embodiment of the present disclosure, the display module 260 displays the user interfaces corresponding to the similar group accounts, the user interface corresponding to the user account, and the user interface corresponding to the account to be compared with the user account, with at least one of different colors, sizes, and images.

Further, the display module 260 determines a rank of the user account among all the similar group accounts, and can display the rank. In addition, the display module 260 can display burnt calories of the user account based on each date, burnt calories based on each week, and burnt calories based on each month.

According to various embodiments of the present disclosure, the devices (for example modules or their functions) or methods are implemented by computer program instructions stored in a computer-readable storage medium. In the case that the instructions are executed by at least one processor (for example processor 120), the at least one processor executes the functions corresponding to the instructions. The computer-readable storage medium can be the memory 130.

At least a part of the programming module can be implemented (for example executed) by the processor 120. At least a part of the programming module can include modules, programs, routines, sets of instructions, and processes for executing the at least one function.

The computer-readable storage medium includes magnetic media such as a floppy disk and a magnetic tape, optical media including a Compact Disc (CD) ROM and a Digital Video Disc (DVD) ROM, a magneto-optical media such as a floptical disk, and the hardware device designed for storing and executing program commands such as ROM, RAM, and flash memory. The programs commands include the language code executable by computers using the interpreter as well as the machine language codes created by a compiler. The aforementioned hardware device can be implemented with one or more software modules for executing the operations of the various exemplary embodiments of the present disclosure.

The module or programming module of the present disclosure can include at least one of the aforementioned components with omission of some components or addition of other components. The operations of the modules, programming modules, or other components can be executed in series, in parallel, recursively, or heuristically. Also, some operations can be executed in different order, omitted, or extended with other operations.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A method of displaying health information by an electronic device, the method comprising:
   executing an application providing at least one piece of health-related information;
   identifying a user account pre-stored in the application and receiving health data of the user account, wherein the health data of the user account includes pre-stored basic health data and a health state measurement data of the user account;
   receiving a plurality of health state measurement data of other user accounts subscribed to the application from a host device;
   determining a similar group based on the health data of the user account and the plurality of health state measurement data of the other user accounts; and
   displaying the health data of the user account and the plurality of health state measurement data of the other user accounts corresponding to the determined similar group,
   wherein the similar group is changed at every predetermined period.

2. The method of claim 1, further comprising:
   determining at least one health comment among pre-stored health comments based on the health state measurement data of the user account and the plurality of health state measurement data of the other user accounts; and
   displaying the determined health comment.

3. The method of claim 1, wherein the displaying of the health data of the user account and the plurality of health state measurement data of the other user accounts corresponding to the similar group comprises:

comparing the health state measurement data of the user account with the plurality of health state measurement data of the other user accounts; and displaying a user interface corresponding to the user account and a user interlace corresponding to the other user account, based on a comparison result of the health state measurement data.

4. The method of claim 3, wherein the displaying of the user interface corresponding to the user account and the user interface corresponding to the other user account, based on the comparison result of the health state measurement data comprises:

displaying the user interface corresponding to the user account and the user interface corresponding to the other user account, with at least one of different colors, sizes, and images; and displaying a user interface indicating that a result value of one of the user account and the other user account is higher than that of the other based on result values of health state measurement data included in the health state measurement data of the user account and the plurality of health state measurement data of the other user accounts.

5. The method of claim 3, wherein the comparing of the health state measurement data of the user account with the plurality of health state measurement data of the other user accounts comprises comparing at least one piece of calorie data, muscle amount data, and body fat data of the user account with at least one corresponding piece of calorie data, muscle amount data, and body fat data of the other user account, during a predetermined period.

6. An electronic device comprising:

a communication module configured to identify a user account pre-stored in an application providing at least one piece of health-related information, receive health data of the user account, and receive a plurality of health state measurement data of other user accounts subscribed to the application from a host device, wherein the health data of the user account includes pre-stored basic health data and a health state measurement data of the user account;

a control module configured to activate the application, determine a similar group based on the health data of the user account and the plurality of health state measurement data of the other user accounts; and a display module configured to display the health data of the user account and the plurality of health state measurement data of the other user accounts corresponding to the determined similar group, wherein the similar group is changed at a predetermined period.

7. The electronic device of claim 6, wherein the control module is configured to determine at least one health comment among pre-stored health comments based on the health state measurement data of the user account and the plurality of health state measurement data of the other user accounts, and control the display module to display the determined health comment.

8. The electronic device of claim 6, wherein the control module is configured to compare the health state measurement data of the user account with the plurality of health state measurement data of the other user accounts subscribed to the application, and display a user interface corresponding to the user account and a user interface corresponding to the other user account, based on a comparison result of the health state measurement data.

9. The electronic device of claim 8, wherein the display module is configured to display the user interface corresponding to the user account and the user interface corresponding to the other user account, with at least one of different colors, sizes, and image, or display a user interface indicating that a result value of one of the user account and the other user account is higher than that of the other based on result values of health state measurement data included in the health state measurement data of the user account and the plurality of health state measurement data of the other user accounts.

10. The electronic device of claim 8, wherein the control module is configured to compare at least one piece of calorie data, muscle amount data, and body fat data of the user account with at least one corresponding piece of calorie data, muscle amount data, and body fat data of the other user account, during a predetermined period.

11. A plurality of instructions stored on a non-transitory computer readable medium, the plurality of instructions configured to, when executed by a processor, cause the processor to:

identify a user account pre-stored in an application providing at least one piece of health-related information, receive health data of the user account, and receive a plurality of health state measurement data of other user accounts subscribed to the application from a host device, wherein the health data of the user account includes pre-stored basic health data and a health state measurement data of the user account;

activate the application;

determine a similar group based on the health data of the user account and the plurality of health state measurement data of the other user accounts; and cause a display module to display the health data of the user account and the plurality of health state measurement data of the other user accounts corresponding to the determined similar group, wherein the similar is changed at a predetermined period.

12. The plurality of instructions of claim 11, wherein the plurality of instructions is configured to cause the processor to determine at least one health comment among pre-stored health comments based on the health state measurement data of the user account and the plurality of health state measurement data of the other user accounts, and control the display module to display the determined health comment.

13. The plurality of instructions of claim 11, wherein the plurality of instructions is configured to cause the processor to compare the health state measurement data of the user account with the plurality of health state measurement data of the other user accounts, and display a user interface corresponding to the user account and a user interface corresponding to the other user accounts, based on a comparison result of the health state measurement data.

14. The plurality of instructions of claim 13, wherein the plurality of instructions is configured to cause the processor to display the user interface corresponding to the user account and the user interface corresponding to the other user account, with at least one of different colors, sizes, and image, or display a user interface indicating that a result value of one of the user account and the other user account is higher than that of the other based on result values of health state measurement data included in the health state measurement data of the user account and the plurality of health state measurement data of the other user accounts.

15. The plurality of instructions of claim 13, wherein the plurality of instructions is configured to cause the processor to compare at least one piece of calorie data, muscle amount data, and body fat data of the user account with at least one corresponding piece of calorie data, muscle amount data, and body fat data of the other user account, during a predetermined period.

* * * * *